(12) United States Patent
Ley et al.

(10) Patent No.: US 6,360,129 B1
(45) Date of Patent: Mar. 19, 2002

(54) MANNITOL/HYDROGEL CAP FOR TISSUE-INSERTABLE CONNECTIONS

(75) Inventors: Gregory R. Ley, New Brighton; Larry L. Hum, Cottage Grove, both of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/459,782

(22) Filed: Dec. 13, 1999

(51) Int. Cl.[7] .................................................. A61N 1/00
(52) U.S. Cl. ........................ 607/127; 607/120; 600/375; 604/57
(58) Field of Search ........................ 607/119–120, 127, 607/131; 600/375; 604/175, 57

(56) References Cited

U.S. PATENT DOCUMENTS

| | | | |
|---|---|---|---|
| 3,220,960 A | 11/1965 | Wichterle et al. | 260/2.5 |
| 3,520,949 A | 7/1970 | Shepard et al. | 260/857 |
| 3,551,556 A | 12/1970 | Kliment et al. | 424/21 |
| RE27,401 E | 6/1972 | Wichterle et al. | 260/2.5 R |
| 3,948,863 A | 4/1976 | Akamatsu et al. | 260/78 A |
| 4,026,303 A | 5/1977 | Babotai | 128/418 |
| 4,178,361 A | 12/1979 | Cohen et al. | 424/22 |
| 4,217,901 A | 8/1980 | Bradstreet et al. | 128/290 R |
| 4,295,987 A | 10/1981 | Parks | 252/194 |
| 4,347,198 A | 8/1982 | Ohkada et al. | 264/2.3 |
| 4,467,012 A | 8/1984 | Pedersen et al. | 428/248 |
| 4,507,438 A | 3/1985 | Obayashi et al. | 525/119 |
| 4,783,510 A | 11/1988 | Saotome | 525/329.7 |
| 4,827,940 A | 5/1989 | Mayer et al. | 128/642 |
| 4,950,264 A | 8/1990 | Osborn, III | 604/385.1 |
| 5,080,099 A | 1/1992 | Way et al. | 128/640 |
| 5,145,906 A | 9/1992 | Chambers et al. | 524/732 |
| 5,196,456 A | 3/1993 | Nguyen et al. | 522/81 |

(List continued on next page.)

FOREIGN PATENT DOCUMENTS

| | | | |
|---|---|---|---|
| EP | 0216074 | 4/1987 | C08F/261/04 |
| EP | 0337035 | 10/1989 | 607/127 |
| EP | 0683177 | 11/1995 | C08F/8/12 |
| EP | 0761254 | 3/1997 | A61N/1/05 |
| GB | 0299553 | * 11/1928 | |
| JP | 5241309 | 9/1993 | G03C/11/00 |
| JP | 5279416 | 10/1993 | C08F/8/30 |
| JP | 6506244 | 7/1994 | C08G/69/10 |
| JP | 7224163 | 8/1995 | C08G/69/10 |
| JP | 7309943 | 11/1995 | C08G/73/00 |
| JP | 8059820 | 3/1996 | C08G/69/10 |

OTHER PUBLICATIONS

Yin, Y., et al., "Relationship Between Poly(acrylic acid) Gel Structure and Synthesis", In: *Polyelectrolyte Gels—Properties, Preparation, and Applications*, Chapter 6, ACS Symposium Series 480, Washington, D.C., pp. 91–113, (1992).

*Primary Examiner*—Mark Bockelman
(74) *Attorney, Agent, or Firm*—Schwegman, Lundberg, Woessner & Kluth, P.A.

(57) ABSTRACT

A helical element for insertion into tissue comprises a helical element having an insertion end, a protruding end and an open central area within the wire, rods, filaments, cables or the like that form the helix. The helical element has at least its insertion end covered by a cap of a water-soluble or water-dispersible composition. The composition of the cap comprises a water-soluble or water dispersible component having a hydrogel mixed therein. In one embodiment, there is either a hollow area within the composition within the open central area or the material is more porous than the remaining material. The helical element preferably comprises an electrical lead, such as a positive endocardial lead, with an electrode at the protruding or distal end of the lead.

The helical element may comprise any biocompatible material with sufficient structural integrity to provide a secure attachment to tissue in a patient. Where the helical element is also to provide an active (electrically active) function, the composition of the helical element should also be electrically conductive.

25 Claims, 1 Drawing Sheet

U.S. PATENT DOCUMENTS

| | | | |
|---|---|---|---|
| 5,247,068 A | 9/1993 | Donachy et al. | 530/350 |
| 5,250,642 A | 10/1993 | Ahmed et al. | 526/240 |
| 5,284,936 A | 2/1994 | Donachy et al. | 530/350 |
| 5,525,682 A | 6/1996 | Nagamoto et al. | 525/420 |
| 5,531,783 A | 7/1996 | Giele et al. | 607/126 |
| 5,837,007 A | 11/1998 | Altman et al. | 604/127 |
| 5,902,329 A | 5/1999 | Hoffmann et al. | 607/121 |
| 5,919,570 A | 7/1999 | Hostettler et al. | 428/424.8 |
| 5,931,862 A | 8/1999 | Carson | 607/120 |
| 5,951,597 A | 9/1999 | Westlund et al. | 607/126 |
| 5,964,794 A | 10/1999 | Bolz et al. | 607/121 |
| 6,139,538 A * | 10/2000 | Houghton et al. | |

* cited by examiner

MANNITOL/HYDROGEL CAP FOR TISSUE-INSERTABLE CONNECTIONS

BACKGROUND OF THE ART

1. Field of the Invention

The present invention relates to the field of insertable or implantable materials or devices in which the material or device is secured into the tissue of a patient through a helical or screw element which is secured into tissue or the like. In particular, the present invention relates to protective elements such as protective caps over a penetrating or pointed section of the material or device, wherein the protective element is capable of timely removal (as by dissolution) from the penetrating or pointed section during technical (e.g., medical) procedures. Typical devices for use in the present invention are connectors or leads for electrical stimulation or pacing of organs, such as cardiac pacers or defibrillators.

2. Background of the Art

Many therapeutic or protective procedures for patients include the implantation of devices into a patient. Such implantations include drug delivery systems, electrostimulating devices (such as pacemakers or pain reduction devices), monitoring devices, electrical leads, electrodes, sensor elements, etc. These devices often have to be firmly secured within the patient to prevent movement of the device that would defeat or diminish its effectiveness. This is particularly true with electrical leads in pacing or defibrillation devices, which must be precisely located so that electrical stimulation is effective. There are a number of different formats for the securement of electrical leads in patients, including, but not limited to, clips, sutured attachment, corkscrew-like inserts (referred to as helical inserts), and other conventional securement formats found in mechanical systems.

A preferred means of securing leads is the helical insert such as found in the GUIDANT™ Sweet-Tip™ Model 4269 bipolar endocardial lead. This lead comprises a helical element having a base side (proximal end) with an electrode and a sharp tip on an insert side (a distal end) of the element. The pointed end penetrates tissue when a rotating motion is applied to the helical element, causing the element to puncture and or screw into the tissue, advancing the proximal end towards the tissue. The proximal end may have a relatively flat or convex electrical plate, electrode, sensing element (e.g., semiconductor, circuit board, pressure plate, etc.) or contact, and the advancing of the helical element into the tissue brings the contact into firm position with the tissue. In pacing or defibrillating devices, the electrical discharge passes through the electrode and/or into the helical connecting element. In some leads, the helical element is coated with an insulating polymer (which must also be biocompatible) to render the helical element inactive or passive (from the standpoint of discharge). Typical polymer coatings could include polyamides, polyurethanes, silicone resins, polyacrylates, hardened gelatin, and especially poly-para-xylylene (e.g., Parylene C).

U.S. Pat. No. 5,964,794 describes an implantable stimulation electrode for use with an implantable tissue stimulator, in particular a pacemaker, defibrillator, bone or neurostimulator, having a metal substrate body and a coating, applied to the substrate body, for reducing the electrode impedance and/or increasing the tissue comparability, in which an ultrathin, specifically functionalized organic coating forming the entire outer surface of the stimulation electrode is provided, which adheres to the underlying surface as a consequence of irreversible physisorption or covalent chemical bonding. An organic layer is provided on the surface of an implantable stimulation electrode, which layer prevents or at least decisively reduces the nonspecific adsorption of biological macromolecules and is selectively specifically functionalized or functionalizable. Such an effect, which leads to a novel quality of biocompatibility while simultaneously obtaining high phase-boundary capacitance and hence low electrode impedance, is unattainable with the known stimulation electrodes having a metallic or inorganic surface. The term "organic layer" will be used hereinafter to include such a layer having silicon atoms, of the kind that can be formed by reaction with silanes, for instance. An additional functionalization of potential practical significance is that the organic layer has sensor molecules (such as enzymes) such that the stimulation electrode can act as a biosensor electrode. In a further important functionalization, the organic layer has a medicinal active ingredient, in particular an anti-inflammatory medication, which can be exported from the organic layer under diffusion or solution control. In particular, the medicinal active ingredient may be substantially embedded between constituent layers of the multilayer structure. The organic layer is ultrathin; that is, its layer thickness of the organic coating is in the range between 1 and 200 nm, and in certain versions (for instance as a polyelectrolyte multilayer) is preferably in the range between 3 and 50 nm. To assure advantageous electrical properties, and especially little influence on the high phase-boundary capacitance of highly sophisticated stimulation electrodes, even at relatively high layer thicknesses in the aforementioned range, the organic layer in an advantageous embodiment is embodied such that it has a relative dielectric constant of greater than 100 and in particular greater than 300. At very slight layer thicknesses, layers with a relatively low dielectric constant can also be used.

U.S. Pat. No. 5,080,099 describes skin electrodes with hydrogel contact elements as stimulation electrodes for an external defibrillator and/or pacemaker.

A suitable conductive gel 106 would be, for example, an RG 63T hydrogel.

U.S. Pat. No. 5,951,597 describes a coronary sinus lead having an expandable matrix anchor. An intravenous lead for use with a cardiac device for implantation in the coronary venous system of the heart includes a lead body that is adapted to be routed through the vascular system into the coronary sinus with the distal end portion of the lead placed in the great cardiac vein or branch vein. The lead body includes a fixation member disposed just proximal of its tip. The fixation member comprises a radially expandable polymeric matrix that incorporates an osmotic agent so that when placed in a aqueous medium it will swell. Thus, when placed in a cardiac vein, the swelling of the fixation member will anchor the lead against longitudinal displacement due to body motion, blood flow and the beating action of the heart.

U.S. Pat. No. 4,347,198 describes the manufacture of contact lenses where a hydrophilic component, for example N-vinylpyrrolidone, a hydrophobic component, for example methyl methacrylate, a cross-linking agent and an initiator are mixed in a solvent, for example DMSO, and then the whole is cross-linked in a mold. After extraction and equilibration in water, a soft hydrogel contact lens is obtained. Extraction with water is necessary because the solvent and unreacted vinyl monomers have to be removed. Since a polymer swells to different extents, for example in DMSO on the one hand and water on the other, the contact lens assumes its final size only at that stage.

EP 216 074 describes a process for the preparation of hydrogel contact lenses. There, a methacrylate-modified polyvinyl alcohol is used which is copolymerised in DMSO solution with vinyl monomers in a suitable casting mold, for example in the presence of a photoinitiator by irradiation with UV light for approximately 3 hours. After being removed from the mold, the contact lens is extracted with water or physiological saline solution in order to remove the DMSO and unreacted vinyl monomers. In this case too, the contact lens does not receive its final geometry until the final stage owing to the different influences of DMSO and water on its swelling behavior.

U.S. Pat. No. 5,931,862 discloses a continuous sheath of open-celled porous plastic, preferably PTFE, is used on the outside of a medical lead, extending along the lead body and the electrodes. Because the plastic is open-celled, when the pores are filled with saline, the lead can deliver electrical energy through the pores in the plastic. Pore size is chosen to discourage tissue ingrowth while allowing for defibrillation energy delivery and electrical signals through it. The porous plastic has a biocompatible wetting agent applied to it to speed the process of filling the pores with saline. The pores over nonelectrode regions may be filled with a non-conductive or conductive polymer to further prevent tissue ingrowth. Likewise, the conductive portions may have pores filled with a conductive polymer to further prevent tissue ingrowth, such as a hydrogel, for example, polyethylene oxide (PEO).

U.S. Pat. No. 5,919,570 describes a blend of hydrogel and polymer. Slippery, hydrophilic coating compositions of a polyurethane/urea prepolymer adduct intermediate commingled with at least one dissimilar hydrogel polymer precursor, and materials composed of a polymeric plastic or rubber substrate or a metallic substrate with a slippery hydrogel coating of a polyurethane/urea prepolymer adduct intermediate and at least one dissimilar hydrogel thereon, such that the coating composition tenaciously adheres to the substrate, are disclosed. The coating compositions and coated materials are non-toxic and biocompatible, and are ideally suited for use on medical devices, particularly, catheters, catheter balloons and stents. The coating compositions, coated materials and coated devices demonstrate low coefficients of friction in contact with body fluids, especially blood, as well as a high degree of wear permanence over prolonged use of the device. The hydrogel coatings are capable of being dried to facilitate storage of the devices to which they have been applied, and can be instantly reactivated for later use by exposure to water.

U.S. Pat. No. 5,902,329 describes an extractable lead and method for chronic blood contacting use. The new lead contains a hydrogel coating having a thickness increase greater than 10% when hydrated. A thick coating is used to provide a shear layer so that the coating tears during extraction, either at the coating/lead interface, between layers of the coating itself, or at the coating/tissue interface.

Many hydrogels are referred to in the art as superabsorbent polymers (SAP) which are generally polymeric materials containing water-insoluble long chain molecules with a low degree of cross-linking which are capable of forming hydrogel networks. In the presence of water or aqueous solutions such as body fluid, these hydrogel networks swell into a soft, resilient "jelly-like" material. When the swelling fluid is 0.9% saline, urine, or synthetic urine, these polymers may ultimately swell up to about 25–40 times their original weight. On the other hand, pulp fibers have a capacity to swell by a factor of only about 7–10 times by comparison.

The SAP materials are typically produced as granules that may then be mixed with pulp fibers during the formation of the absorbent core. Thus, with such highly absorbent granular material, it becomes possible to design and produce absorbent articles with roughly ½ to ⅓ of the bulkiness of the 100% pulp core. Reduction in volume of this nature is the subject of numerous U.S. Patents including for example, U.S. Pat. Nos. 4,950,264 (Osborn); 4,467,012 (Pederson); and 4,217,901 (Bradstreet), In addition, processes for obtaining a hydrogel by cross-linking an acidic amino acid were reported by Akamatsu et al. in U.S. Pat. No. 3,948,863 (corres. JP Kokoku 52-41309) and Iwatsuki et al. in JP Kokai 5-279416. Further, use of cross-linked amino acid polymers as superabsorbent polymers was reported by Sikes et al. in JP PCT Kokai 6-506244 (corres. U.S. Pat. Nos. 5,247,068 and 5,284,936), Suzuki et al. in JP Kokai 7-309943 and Harada et al. in JP Kokai 8-59820. Superabsorbent polymers having high saline-absorbency are disclosed in JP Kokai 7-224163.

These types of devices may be inserted into a patient by a number of different medical procedures. The less invasive or traumatic the procedure, the more desirable is that procedure. For example, although the electrodes may be inserted by open chest surgery, the delivery of the electrode through catheterization techniques through arteries or veins is much more preferred. The difficulties involved with passing a sharp element through the vasculature of a patient can be readily appreciated, especially where the path can be tortuous or partially clogged with deposits. To avoid damage to the patient, the GUIDANT™ Sweet-Tip™ Model 4269 and the GUIDANT™ Sweet Pico Tip bipolar endocardial leads provide a mannitol cap over the helical element in the lead. The mannitol cap provides a protective cover for the helical element which prevents the point of the helical element from scraping or puncturing interior walls of the vasculature or other tissue during introduction of the element to the patient. The mannitol effectively dissolves during the procedure, depending on the placement of the lead and other environmental factors, usually over the course of about 4 to 10 minutes. With certain lead designs and target locations, the leads can be inserted and used when there is only partial dissolution of the caps. This practice of providing caps on the leads has been effective in preventing damage to the patient during the introduction of the lead. Improper use of the lead, as by unauthorized immediate insertion, can lead to dislodgement or unsatisfactory pacing, which could occur with the misuse of any lead.

Other formats for delivering helical or barbed elements to secure an electrode into contact with appropriate tissue have utilized securing elements which are in a retracted position within the end of the delivered electrode. The retracted element is advanced into an exposed and operative position after positioning of the distal end of the electrode element within the patient. Advancement and exposure of the retracted element may be effected, for example, by winding or screwing a helical element through a hole in the most forward area of the electrode or by simply advancing a straight element through a hole.

There have been at least two areas identified by the present inventors where improvements may be made in the use of mannitol caps in the protection of helical leads or securing elements. Because of the physical shape of the helical element, mannitol present within the core of the helix tends to be dissolved out more slowly than desirable from within the helix and adjacent any electrode at the proximal end of the helical element. Additionally, any slowly dissolving mannitol that does remain within the confines or central area of the helix may have a tendency to slow down the advance of the helical element through the tissue until all of the mannitol in the core area has been removed. The lack of consistent rates of dissolution of the caps from the helical element, for example where the lead was prematurely positioned into soft tissue, tends to require surgeons to wait for a maximum length of time to provide assurance of the cap dissolution and proper electrical contact. Although neither of these considerations affect the in place performance of the connected leads, the reduction in procedural time by reducing or eliminating these effects is desired.

U. S. patent application Ser. No. 09/056,283 filed Apr. 7, 1998, now U.S. Pat. No. 6,091,978 describes helical connectors are provided with protective caps of an aqueous soluble or aqueous dispersible material wherein there is a hollow area or porous area of said material in a region within the enclosing region of the helix, with the aqueous soluble/dispersible materials including sugars such as mannitol. Although this construction significantly assists in the function of the removal of the cap, the beneficial effect is clearly dependent upon the ability to consistently shape and form specific designs in the cap structure. It is desirable to be able to effect dissolution parameters or rates that may be more generally controlled, as by selection of unique materials for use in the cap.

SUMMARY OF THE INVENTION

Caps for insertable leads, particularly for helical electrical connector leads comprise a blend or mixture of a first water-soluble or water-dispersible component (e.g., sugar(s) such as mannitol) and a hydrogel. The combination of the two materials provides increased control over dissolution/dispersion rates and the physical strength and characteristics of the cap. The cap material may be solid or may be constructed with specific structural characteristics (hollow, porous, external shaping such as grooves, core shell construction, etc.) to provide a range of physical characteristics.

DETAILED DESCRIPTION OF THE INVENTION

Figure 1:
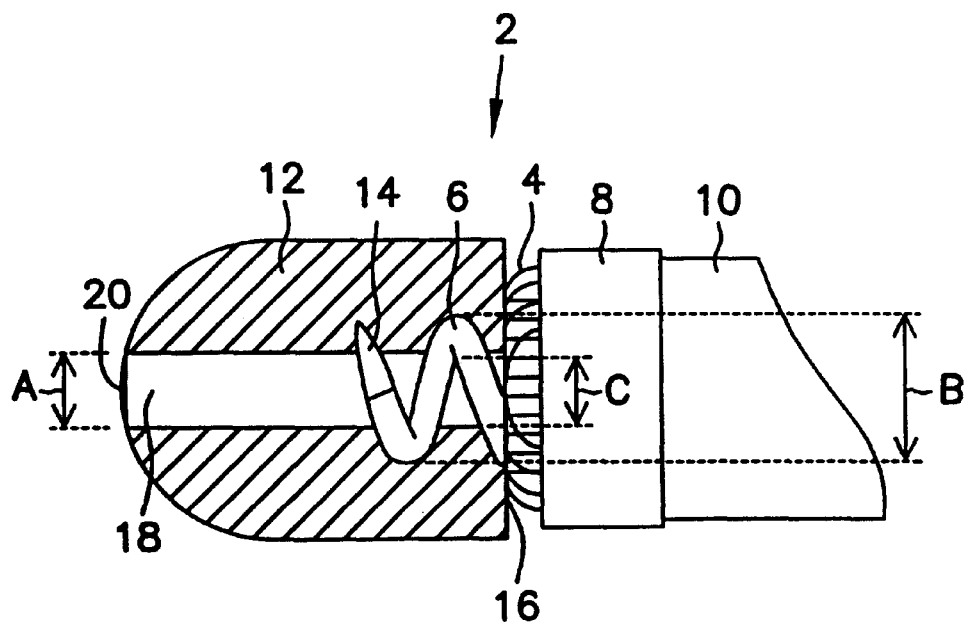
FIG. 1 shows an endocardial lead with a water soluble hollow cap.

The present invention describes a helical element, especially a helical element which can be securely inserted into electrical contact. The helical element for insertion into tissue may comprise, for example, a helical element, an electrical contact, and a support for the electrical contact. The helical element has an insertion end (e.g., an end which is to be inserted to secure the element) and a protruding end. The protruding end (the proximal end with respect to a supporting element) protrudes from or is attached to an electrical contact or is part of the electrical contact. There is an open central area within the wire, rods, filaments, cables or the like that form the helix of the helical element (the central open core of the helix). The helical element has at least its insertion end covered by a cap of a water-soluble or water-dispersible composition. In the embodiment where a more readily dissolvable central portion of the cap is desired, the open area within the helical element may be either free of water-soluble or waterdispersible composition or contains a water-soluble or water-dispersible composition which dissolves more readily than the remainder of the composition which forms the cap. For example, the composition could be porous, fibrillated or the like, and composed of the same or different water-soluble or water-dispersible material that is a component of the cap. The helical element preferably comprises an electrical lead, such as a positive endocardial lead, with an electrode at the protruding or distal end of the lead.

The helical element may comprise any biocompatible material with sufficient structural integrity to provide a secure attachment to tissue in a patient. Where the helical element is also to provide an active (electrically active) function, the composition of the helical element should also be electrically conductive. With these features in mind, a wide range of materials may be selected by the user for the helical element, including, but not limited to, metals, metal oxides, ceramics, polymeric materials, composite materials, reinforced materials, and the like. Metals such as Nitinol™, titanium, silver, gold, platinum, alloys, and the like are preferred.

As previously noted, the helical element may be coated with a protective or insulating layer to render the helical element inactive with respect to pacing discharges. Such coatings should be biocompatible such as polymer coatings including polyamides, polyurethanes, silicone resins, hardened gelatin, and especially poly-para-xylylene (e.g., Parylene C) and ceramic or composite coatings.

The improved cap of the present invention comprises a dispersion or physical mixture of both 1) a water-soluble or water-dispersible component and 2) a hydrogel. By varying the proportions of the two different materials together, the physical and/or dissolution rate properties of the cap can be readily adjusted or prescribed. Although this invention is not limited to a specific mechanism of performance, it may be hypothesized that at least one possible effect of the hydrogel within the cap with the water-soluble or water-dispersible component is to cause a physical stressing of the cap to increase the rate of dissolution. This phenomenon may be viewed as follows. Hydrogels are not truly soluble materials in water, but rapidly swell and expand in contact with water (or aqueous solutions or dispersions such as blood). Therefore, dispersed particles of a hydrogel within a water-soluble or water-dispersible phase (such as a mannitol cap) with rapidly swell and expand, placing physical stress on the mannitol phase, causing the mannitol to separate or crack from the stress, thereby enabling the mannitol to dissolve more rapidly since it is being broken into smaller pieces. By controlling the rate of absorption, the swellable degree, the size of the dispersed particles, and the volume percentage of the hydrogel, the rate of dissolution of the cap and the dissolution profile may be readily controlled and tailored to specific needs.

The water-soluble or water-dispersible component of the composition of the cap material must meet the requirement that it is aqueous-soluble or aqueous-dispersible (blood being the aqueous system of choice for determining these physical properties). Preferably a 0.05 inch edge cube of the material in human blood at normal body temperature with light stirring should dissolve or disperse within ten minutes to meet this requirement. Natural sugars, saccharides, starches, other carbohydrates, polymers and the like are examples of materials which may be used for this cap material. It is particularly desirable that the cap material be non-toxic and preferably be biocompatible or even biodegradable or digestible. For example, mannitol, iditol, glucitol, rabitol, heptitol, octitol, arabinitol, betitol, bornesitiol, dambonitol, inositol, laminitol, ononitol, pinitol, sorbitol, non-crosslinked gelatin, poly(vinyl alcohol), poly(vinylpyrrolidone), soluble acrylates, soluble ethers, and soluble polyesters may be used in the practice of the present invention. Microfibers or biocompatible materials (e.g., microcellulose) held together by water-soluble water-dispersible binders may also be used in the practice of the present invention. Ingredients may also be present within these materials which increase the rate of dissolution, dispersion, or separation of the ingredients in the cap material, as is well known in the pharmaceutical tableting art.

Hydrogels are a well recognized class of polymeric materials. These materials are characterized by their water-insolubility, hydrophilicity, high-water absorbability and swellable properties. Hydrogels may be crosslinked or linear, thermoplastic or thermoset. The molecular components or units or segments of the hydrogel are characterized by a significant portion of hydrophilic components, units or segments, such as segments having ionic species or dissociable species such as acids (e.g., carboxylic acids, phosphonic acids, sulfonic acids, sulfinic acids, phosphinic acids, etc.), bases (e.g., amine groups, proton accepting groups), or other groups that develop ionic properties when immersed in water (e.g., sulfonamides). Acryloyl groups (and to a lesser degree methacryloyl groups) and the class of acrylic polymers, polymer chains containing or terminated with oxyalkylene units (such as polyoxyethylene chains or polyoxyethylene/polyoxypropylene copolymer chains) are also well recognized as hydrophilic segments that may be present within hydrophilic polymers.

Hydrogels are reported in the literature as including at least the following general classes of materials:

Non-crosslinked hydrogels such as physical gels of proteins and polysaccharides (e.g., gelatin), block copolymer hydrogels with blocks selected from hydrophilic blocks and non-hydrophilic blocks (with at least some proportion of hydrophilic blocks being required), copoly(amino acid) hydrogels, polyelectrolyte complexes and polymer blends;

Crosslinked hydrogels such as hydrogels made of natural polymers and/or synthetic polyamino acids (e.g., gelatins crosslinked with conventional gelatin crosslinking agents as well known in the photographic art), interpenetrating hydrogel networks (two distinct polymer chains that are intertwined, with at least one of the polymer chains comprising a hydrophilic polymer), polyester hydrogels and polycaprolactone hydrogels;

Hydrogels with degradable crosslinking agents, such as hydrogels that contain small molecule crosslinking agents or crosslinking agents that are cleaved by aqueous immersion, such as hydrogels crosslinked with N,N'-methylene-bis-acrylamide, azo reagents, sucrose or oligopeptides; and Hydrogels crosslinked with macromolecules, such as polymer chains crosslinked by insulin molecules, vinyl polymers (such as vinyl alcohol) polymerized in the presence of functionalized (e.g., bi-functionally reactive) macromolecules (e.g., hydrogels crosslinked with albumin, hydrogels crosslinked with polysaccharides, and hydrogels with degradable pendant chains).

With regard to the hydrogel forming polymer, certain preferred water insoluble polymeric compositions useful in the present invention are listed below, although the entire class of hydrogel materials known in the art may be used to various degrees. The polymers set forth below and containing acid groups can be, as an option, partially or completely neutralized with alkali metal bases either as the monomer or the polymer or both. While the list below contains many of the preferred polymers which may be used in accordance with the present invention, the present invention is not limited to just these polymers and generally polymers traditionally understood as hydrogels by those skilled in the art can also be used:

a) polyacrylic acid, polymethacrylic acid, polymaleic acid, copolymers thereof, and alkali metal and ammonium salts thereof;

b) graft copolymers of starch and acrylic acid, starch and saponified acrylonitrile, starch and saponified ethyl acrylate, and acrylate-vinyl acetate copolymers saponified;

c) polyvinyl alcohol, polyvinylpyrrolidone, polyvinyl alkylether, polyethylene oxide, polyacrylamide, and copolymers thereof;

d) copolymers of maleic anhydride and alkyl vinylethers; and e) saponified starch graft copolymers of acrylonitrile, acrylate esters, vinyl acetate, and starch graft copolymers of acrylic acid, methylacrylic acid, and maleic acid.

The above exemplary polymers can be used in their linear state, or optionally, cross-linked either during the polymerization or after the core is encapsulated. This cross-linking can be achieved by methods known to those skilled in the art, including the use of a cross-linking agent. This cross-linking can be initiated in the presence of radiation or a chemical free radical initiator.

Polyfunctional cross-linking agents useful in the present invention include epichlorohydrin and related halo epoxy compounds, diglycidyl ether compounds, diisocyanates, polyaldehydes, and polyfunctional amines and imines.

Polyfunctional ethylenically unsaturated cross-linking agents include N,N',-methylene bisacrylamide, trimethylolpropanetriacrylate, ethylene glycol bismethacrylate, polyethylene glycol bismethacrylate, and divinyl benzene. The use of additional polymer cross-linking agents to modify the properties of gel forming polymers is well known and described in U.S. Pat. No. 4,783,510 as well as by Yin, Y., Polyelectrolyte Gels, Chapter 6, American Chemical Society, 1992, both incorporated herein by reference.

One such material is the synthetic hydrogel matrices which comprise water insoluble, but water swellable crosslinked hydrophilic polymers. Particularly suitable hydrophilic monomers for synthesizing hydrogels are known to those skilled in the art and include the hydrophilic monomers/polymers described in U.S. Pat. Nos. 4,178,361 and 3,551,556, the disclosures of which are expressly incorporated herein by reference.

One of the useful properties of hydrogels is their ability to absorb water and swell without dissolution of the matrix. As the hydrogel swells, the pore size of the hydrogel increases which enhances uptake of aqueous solutions and the diffusion of compounds out of the hydrogel. These properties have allowed use of hydrogels as controlled drug release systems and as absorbent materials. However, the rate of swelling of dried hydrogels upon exposure to an aqueous solution is limited by diffusion of water into the glassy polymer matrix. Conventional dried hydrogels have relatively small pore sizes resulting in slow swelling and release or absorption of liquids. The size of the pores in the hydrogel can be a factor used in the selection of hydrogels with the appropriate properties for the specific removable caps in the practice of the present invention. The larger the pore size, the generally higher rate of initial swelling a hydrogel undergoes.

Hydrogel forming polymers and methods of preparation are known in the art and these polymers can be used in the present invention including the polymers in which divalent cations are used as cross-linking agents as set forth in U.S. Pat. Nos. 4,507,438; 5,145,906; 5,196,456; 5,250,642; and 4,295,987, all of which are incorporated herein by reference. These materials are synthesized by conventional polymerization techniques, beginning with unsaturated monomers.

Among the many hydrogel polymers which are useful as matrix polymers include poly(hydroxyalkyl methacrylate)s of which poly-(2-hydroxyethyl methacrylate), poly(glyceryl methacrylate) and poly(hydroxypropyl methacrylate) are well-known and identified in the literature as (P-HEMA), (P-GMA) and (P-(HPMA), respectively. Other hydrogel polymers include poly(acrylamide), poly(methacrylamide), poly(N-vinyl-2-pyrrolidine), and poly(vinyl alcohol), hydroxypropyl guar, high molecular weight polypropylene glycol or polyethylene glycol, and the like. It is known to produce sparingly cross-linked, water-insoluble but hydrophilic polymers which can be used as carriers for biologically active, at least slightly water-soluble substances by copolymerization of a major amount of hydrophilic mono-olefinic monomers and a minor amount ranging between 0.01 and 15% of said mono-olefinic monomers, of a low molecular weight cross-linker. As mono-olefinic monomers, particularly monoesters of acrylic or methacrylic acid with polyfunctional alcohols, such as ethyleneglycol monomethacrylate, and as cross-linking agents particularly diesters of said acids with said alcohols, such as ethyleneglycol bis-methacrylate are used and the copolymerization is carried out in the presence of water, see U.S. Pat. No. 3,220,960 or a water-free system, see U.S. Pat. No. 3,520, 949. Low molecular as well as macromolecular, water-soluble substances, such as polyethyleneoxide monomethacrylate together with a minor amount of the corresponding bis-methacrylate have been used (see U.S. Pat. No. 3,220,960) as monomers and cross-linking agents. The water-insoluble, but hydrophilic copolymers and the process for their production have been modified in several directions and adapted to specific purposes, e.g. the production of soft contact lenses, U.S. Pat. No. 3,220,960 and Reissue No. 27,401, and the copolymerization in the presence of linear polyamide resin in order to improve or modify the mechanical properties of shaped bodies formed from the obtained polymers, U.S. Pat. No. 3,520,949.

Non-limiting examples of the unsaturated monomers used as a starting material include those polymerizable monomers known to be soluble in water. Examples of these unsaturated monomer are:

monomers containing an acid group, such as acrylic acid, beta-acryloyloxypropionic acid, methacrylic acid, crotonic acid, maleic acid, maleic anhydride, fumaric acid, itaconic acid, cinnamic acid, sorbic acid, 2-(meth)acryloylethane sulfonic acid, 2-(meth)acryloylpropane sulfonic acid, 2-(meth)acrylamido-2-methylpropane sulfonic acid, vinyl sulfonic acid, styrene sulfonic acid, allyl sulfonic acid, vinyl phosphonic acid and 2-(meth)acryloyloxyethyl phosphate, and alkaline metal salts and alkaline earth metal salts, ammonium salts, and alkyl amine salts thereof;

dialkyl amino alkyl(meth)acrylates, such as N,N-dimethylaminoethyl(meth)acrylate and N,N-dimethylaminopropyl(meth)acrylate, and quaternary compounds thereof (for example, a reaction product produced with alkylhalide, and a reaction product produced with dialkyl sulfuric acid);

dialkyl amino hydroxyalkyl(meth)acrylates, and quaternary compounds thereof;

N-alkyl vinyl pyridine halide;

hydroxyalkyl(meth)acrylates, such as hydroxymethyl (meth)acrylate, 2-hydroxyethyl(meth)acrylate, and 2-hydroxypropyl (meth)acrylate;

acrylamide, methacrylamide, N-ethyl (meth)acrylamide, N-n-propyl(meth)acrylamide, N-isopropyl(meth)acrylamide, N,N-dimethyl (meth)acrylamide, 2-hydroxyethyl (meth)acrylate, 2-hydroxypropyl (meth)acrylate, methoxypolyethylene glycol (meth)acrylate, polyethylene glycol mono(meth)acrylate, vinylpyridine, N-vinylpyrrolidone, N-acryloyl piperidine, and N-acryloyl pyrrolidine;

vinyl acetate; and alkyl (meth)acrylates, such as methyl (meth)acrylate, and ethyl (meth)acrylate.

These monomers may be used individually, or in combination.

Among the above-exemplified monomers, unsaturated monomers containing an acrylate monomer as a chief constituent are preferred because the resulting water-absorbent resins have significantly improved water absorption characteristics. Here, the preferred acrylate monomers includes at least acrylic acids and/or water-soluble salts of acrylic acids. The water-soluble salts of acrylic acids are alkaline metal salts, alkaline earth metal salts, ammonium salts, hydroxy ammonium salts, amine salts and alkyl amine salts of acrylic acids having a neutralization rate within a range of from 30 mole percent to 100 mole percent, more preferably within a range of from 50 mole percent to 99 mole percent. Among the exemplified water-soluble salts, sodium salt and potassium salt are more preferred. These acrylate monomers may be used individually or in combination.

When the unsaturated monomer contains an acrylate monomer as a chief constituent, the amount of monomers other than the acrylate monomer is preferably less than 40 weight percent, more preferably less than 30 weight percent, and most preferably less than 10 weight percent of the total unsaturated monomer. By using the monomers other than the acrylate monomer in the above mentioned ratio, the water absorption characteristics of the resulting water-absorbent resin are further improved, and the water-absorbent resin can be obtained at further reduced costs.

As a cross-linking agent used for polymerizing the unsaturated monomer in the present invention, for example, the following compounds are listed. Compounds having a plurality of vinyl groups in a molecule. Compounds having at least one vinyl group in a molecule and at least one functional group reactive with a carboxyl group in the unsaturated monomer. Compounds having in a molecule a plurality of functional groups reactive with the carboxyl group. These cross-linking agents may be used individually, or in combination.

Examples of the compounds having a plurality of vinyl groups in a molecule are N,N'-methylene bis(meth)acrylamide, (poly)ethylene glycol di(meth)acrylate, (poly)propylene glycol di(meth)acrylate, trimethylolpropane tri(meth)acrylate, trimethylolpropane di(meth)acrylate, glycerine tri(meth)acrylate, glycerine acrylate methacrylate, ethyleneoxide denaturated trimethylolpropane tri(meth)acrylate, pentaerythritol tetra(meth)acrylate, dipentaerythritol hexa(meth)acrylate, N,N-diallyl acrylamide, triallyl cyanurate, triallyl isocyanurate, triallyl phosphate, triallylamine, diallyloxy acetate, N-methyl-N-vinyl acrylamide, bis(N-vinyl carboxylic amide), and poly(meth)allyloxy alkanes such as tetraallyloxy ethane.

As the compound having at least one vinyl group in a molecule and at least one functional group reactive with the carboxylic group, for example, ethylene unsaturated compounds having at least one hydroxyl group, epoxy group or cationic group can be used. Example of such compounds are glycidyl (meth)acrylate, N-methylol acrylamide, and dimethylaminoethyl(meth)acrylate.

As the compound having a plurality of functional groups reactive with the carboxyl group in a molecule, for example, compounds having at least two hydroxyl groups, epoxy groups, cationic groups or isocyanate groups can be used. Example of such compounds are (poly)ethylene glycol diglycidyl ether, glycerol diglycidyl ether, ethylene glycol, polyethylene glycol, propylene glycol, glycerin, pentaerythritol, ethylenediamine, ethylene carbonate, polyethylene imine, and ammonium sulfate.

Among the exemplified cross-linking agents, preferred compounds are water-soluble compounds having a plurality of vinyl groups in a molecule, such as N,N'-methylene bis(meth)acrylamide, (poly)ethylene glycol di(meth)acrylate, (poly)propylene glycol di(meth)acrylate, trimethylolpropane tri(meth)acrylate, trimethylolpropane di(meth)acrylate, glycerine tri(meth)acrylate, glycerine acrylate methacrylate, ethyleneoxide denaturated trimethylolpropane tri(meth)acrylate, pentaerythritol tetra(meth)acrylate, dipentaerythritol hexa(meth)acrylate, triallyl cyanurate, triallyl isocyanurate, triallyl phosphate, triallylamine, and poly (meth)allyloxy alkane.

The amount of the cross-linking agent with respect to the unsaturated monomer varies depending on a combination of unsaturated monomer and cross-linking agent. However, the cross-linking agent is used in an amount ranging preferably from 0.0001 weight parts to 10 weight parts, more preferably from 0.001 weight parts to 5 weight parts, most preferably from 0.01 weight parts to 2 weight parts, based on 100 parts by weight of the unsaturated monomer. When the amount of cross-linking agent exceeds 10 weight parts, such unfavorable results are shown that the absorbent capacity of the resulting water-absorbent resin is lowered, and foaming by a blowing agent, to be described later, becomes insufficient. On the other hand, when the amount of crosslinking agent is less than 0.0001 weight parts, such unfavorable results are exhibited that the absorption rate and the gel strength of the resulting water-absorbent resin are lowered, the water soluble component content increases, and the control of foaming by a blowing agent is difficult. If the unsaturated monomer is polymerized without using a blowing agent, the water absorption characteristics of the resulting water-absorbent resin and various properties of the water-absorbent resin after absorption become unsatisfactory.

When polymerizing the unsaturated monomer under the presence of a crosslinking agent, it is preferred to use an aqueous solution as the unsaturated monomer and the crosslinking agent in order to improve the water absorption characteristics of the resulting water-absorbent resin and to achieve efficient foaming by a blowing agent. Namely, water is preferably used as a solvent. The concentration of the unsaturated monomer in the aqueous solution (hereinafter referred to as the aqueous monomer solution) is exemplified in a non-limiting manner within this description as preferably but not exclusively including a range of from 20 weight percent to 65 weight percent, more preferably from 25 weight percent to 60 weight percent, most preferably from 30 weight percent to 45 weight percent. If the concentration of the unsaturated monomer is less than 20 weight percent, the water-soluble component content in the resulting water-absorbent resin may increase, and the absorption rate may not be improved because foaming by the blowing agent is insufficient. On the other hand, if the concentration of the unsaturated monomer exceeds 65 weight percent, it may be difficult to control the reaction temperature and the foaming by the blowing agent.

It is also possible to use water and an organic solvent soluble in water together as a solvent for the aqueous monomer solution. Examples of the organic solvent are methyl alcohol, ethyl alcohol, acetone, dimethyl sulfoxide, ethylene glycol monomethyl ether, glycerin, (poly)ethylene glycol, (poly)propylene glycol, and alkylene carbonate. These organic solvents may be used individually, or in combination.

The particles of the hydrogel may also be prepared as a foamed particle. In this case, the amount of the organic solvent may be controlled so that the average particle diameter of the blowing agent dispersed is within a range of from 1 to 100 micrometers. More specifically, the amount of the organic solvent is preferably not higher than 40 percent by weight of water, more preferably not higher than 20 weight percent, most preferably not higher than 10 weight percent.

The blowing agent used when polymerizing the unsaturated monomer in the present invention is in particle form, and is a compound which is insoluble or slightly soluble in water and in the organic solvent and is solid at normal temperatures.

Examples of such a blowing agent are:

organic compounds, such as azodicarbonamide, azobisisobutyronitrile, barium azodicarboxylate, dinitrosopentamethylenetetramine, 4,4'-oxybis(benzene sulfonyl hydrazide), p-toluenesulfonyl hydrazide, diazoaminobenzene, N,N'-dimethyl-N,N'-dinitrosoterephthalamide, nitrourea, acetone-p-toluenesulfonyl hydrazone, p-toluenesulfonyl azide, 2,4-toluenedisulfonyl hydrazide, p-methylurethane benzene sulfonyl hydrazide, trinitroso trimethylene triamine, p-toluenesulfonyl semicarbazide, oxalyl hydrazide, nitroguanidine, hydroazocarbonamide, trihydrazino triamine, azo-bis formamide, benzenesulfonyl hydrazide, benzene-1,3-disulfonyl hydrazide, diphenyl sulfone-3,3'-disulfonyl hydrazide, 4,4'-oxybis(benzene sulfonyl hydrazide), sulfone hydrazide, malonic acid and salts thereof, and carbamic acid and salts thereof, acrylic acid salts of azo-compounds containing an amino group. The unsaturated monomer in the aqueous monomer solution in which the blowing agent is dispersed can be polymerized by a known method. The polymerization method is not particularly limited, and various methods can be used. Examples include radical polymerization using a radical polymerization initiator, irradiation-induced polymerization, electron radiation-induced polymerization, and ultraviolet-induced polymerization using a photosensitizer. Among these methods, radical polymerization is more preferred because this method can quantitatively and perfectly polymerize the unsaturated monomer.

As for the radical polymerization step, there are various polymerization methods, such as aqueous solution polymerization, cast polymerization which is performed within a mold, thin-layer polymerization which is performed on a belt conveyer, polymerization which is performed while making generated hydrogel polymer into small pieces, reversed-phase suspension polymerization, reversed-phase emulsion polymerization, precipitation polymerization, and bulk polymerization. Among these polymerization methods, the aqueous solution polymerization which polymerizes the unsaturated monomer in the form of aqueous solution is more preferred because the polymerization temperature can be easily controlled.

The aqueous solution polymerization of the unsaturated monomer may be performed either continuously or batchwise, or may be performed under suction, pressure, or atmospheric pressure. The polymerization is preferably performed in the flow of inactive gas, such as nitrogen, helium, argon, or carbon dioxide gas.

When performing the aqueous solution polymerization, it is preferred to dissolve or disperse a radical polymerization initiator in an aqueous monomer solution in advance. Examples of the radical polymerization initiator include:

- peroxides, such as ammonium persulfate, potassium persulfate, sodium persulfate, hydrogen peroxide, benzoyl peroxide, cumene hydroperoxide, and di-t-butyl peroxide;
- redox initiators formed by combining the above-mentioned peroxides and reducing agents, such as sulfite, bisulfite, thiosulfate, formamidine sulfinic acid, and ascorbic acid;
- acrylic acid salts of azo-compound containing an amino group represented by general formula (1) or (2) above; and
- azo polymerization initiators, such as hydrochlorides of the azo-compound containing an amino group. These radical polymerization initiators may be used individually, or in combination.

The amount of the radical polymerization initiator with respect to the unsaturated monomer is varied depending on the combination of the unsaturated monomer and the radical polymerization initiator. However, the amount of the radical polymerization initiator to be used is within a range of preferably from 0.0005 weight parts to 5 weight parts, more preferably from 0.005 weight parts to 2.5 weight parts, based on 100 parts by weight of the unsaturated monomer. If the amount of the radical polymerization initiator is less than 0.0005 weight parts, the amount of unreacted unsaturated monomers increases, causing an unfavorable increase of the residual monomer content in the resulting water-absorbent resin. On the other hand, if the amount of the radical polymerization initiator exceeds 5 weight parts, an unfavorable increase of the water-soluble component content in the resulting water-absorbent resin occurs.

Although the temperature at the initiation of polymerization varies depending on the type of a radical polymerization initiator used, it is preferably within a range of from 0° C. to 40° C., more preferably from 10° C. to 30° C. Similarly, although the polymerization temperature during the reaction varies depending on the type of a radical polymerization initiator used, it is preferably within a range of from 40° C. to 120° C., more preferably from 50° C. to 110° C. If the temperature at the initiation of polymerization or the polymerization temperature during the reaction is outside of the above-mentioned range, unfavorable results may be exhibited. For example, the residual monomer content in the resulting water-absorbent resin increases, the control of foaming by a blowing agent becomes difficult, and the absorbent capacity of the water-absorbent resin is lowered because of an excessive self-cross-linking reaction.

An example of the complete synthesis of a hydrogel, for example, is as follows: First, 375 parts acrylic acid, 5,290 parts aqueous 37 percent sodium acrylate solution, 6.3 parts polyethylene glycol diacrylate, and 808 parts water were mixed to prepare an aqueous monomer solution. Namely, the aqueous monomer solution is an aqueous 35.5 percent acrylate monomer solution having a neutralization rate of 85 mole percent.

Dissolved oxygen was removed by bubbling a nitrogen gas into the solution while keeping the temperature of the aqueous monomer solution at 25° C. Next, 52 parts aqueous 10 percent 2,2'-azo-bis-(2-methyl propionamidine) dihydrochloride solution was added while agitating the aqueous monomer solution. Thereafter, the aqueous solution was agitated at 25° C. under the flow of nitrogen. About 2.5 minutes later from the initiation of agitation, the aqueous solution appeared cloudy or white, and 2,2'-azo-bis(2-methyl propionamidine)diacrylate in the form of white fine particles with an average particle diameter of 9 millimicrons was generated. The 2,2'-azo-bis(2-methyl propionamidine) diacrylate was evenly dispersed in the aqueous monomer solution.

At this point, 36 parts aqueous 10 percent sodium persulfate solution and 1.7 parts aqueous 1 percent L-ascorbic acid solution were added while agitating the aqueous monomer solution. After the addition, the aqueous monomer solution continued to be agitated. About 30 seconds after the addition of aqueous sodium persulfate solution, polymerization of the acrylate monomer was initiated. As a result, a hydrogel having cells was obtained. The resulting hydrogel having cells was removed, and the same operations as in Example 1 were performed to produce a water-absorbent resin. The average pore diameter of the water-absorbent resin was 100 micrometers. Moreover, various physical properties of the water-absorbent resin were measured by the above-mentioned methods. The water retention capacity was 38 g/g, the residual monomer content was 270 ppm, the water-soluble component content was 9 percent, the dispersion rate was 24 seconds, the dry touch was 4.0 g, and the absorbent capacity under pressure was 10 g/g.

As noted above, the removable cap of the present invention comprises a physical admixture of the water-soluble/water-dispersible component and the hydrogel. The range of blends of the materials will depend upon the relative properties of the two materials and the ultimate properties desired in the cap. A general range for practice of the invention would include from about 0.5% to 90% by weight hydrogel to the water-soluble/water-dispersible component. More narrow ranges that could be used include 0.5% to 80%, 1,0% to 80%, 2% to 80%, and 5% to 50% by weight hydrogel to the water-soluble/water-dispersible component. The materials may be combined in any physical admixture procedure. Specific methods of combination include at least the following. The water-soluble/water-dispersible component may be dissolved.

The hydrogel is usually provided as a particulate material, which tends to be a form of the hydrogel that is conveniently found in commercial supplies. The hydrogel is combined in any convenient method with the water-soluble or water-dispersible component. This may be done in various ways, including but not limited to the following. Particles of hydrogel may be mixed with particles of the water-soluble or water-dispersible component. The particles may be physically mixed, and a solvent used to dissolve the water-soluble or water-dispersible component. The solvent is then evaporated, leaving the hydrogel dispersed within the water-soluble or water-dispersible component.

The water-soluble or water-dispersible component (e.g., a polymer system or solution of the carbohydrate such as mannitol) may be provided in a solvated or liquid carrier dispersed form, and the hydrogel particles are mixed with the system. The solvent is then evaporated from the hydrogel/water-soluble component system. It is desirable to avoid using water or aqueous systems as the carrier for the water-soluble or water-dispersible component, as this would cause swelling of the hydrogel and would require longer drying times than could be effected with a non-aqueous carrier system.

The hydrogel may be placed into the water-soluble or water-dispersible component in any convenient form, with particles preferred, although fibrils, fibers, and strips may also be provided. The dimensions of the hydrogel units in the water-soluble or water-dispersible component may also be varied with desired physical effects. Fibers may be used, for example, with dimensions of from 0.5 to 50 denier in a dry state. Particles may be used in non-limiting dimensions of from 0.5 micrometers to 1 or 2 mm. The particles may be used within a narrower range of, for example only, of from 0.5 to 100 micrometers, or from 1 to 75 micrometers.

It is also desirable in some circumstances to have the cap material carry active or therapeutic ingredients. For example, it is particularly desirable for the cap to carry anti-inflammatants, antibiotics, antiarrhythmic medication, and the like within the composition. These can thereby be locally delivered as the helical device is inserted into the patient and as the cap, e.g., mannitol, dissolves.

FIG. 1 shows an electrode element 2 according to the present invention. The electrode element 2 comprises an electrode 4 having a helical securement element 6. The electrode 4 is carried on a collar or support 8 which is in turn carried on a catheter or lead body 10 for delivery. An aqueous-soluble or dispersible cap 12 covers the helical element 6 and especially a pointed end 14 on the helical element 6. The cap 12 also abuts or lies flat against the contact surface 16 of the electrode 4. A hollow core 18 within the cap 12 is shown. The hollow core 18 has an outside diameter A which is less than the outside diameter B of the helical element 6. This assures that the cap 12 is retained against movement away from the electrode 4. There may optionally be, but not preferably, a cover layer 20 over the opening to the hollow core 18 to prevent tearing of the cap or collection of unwanted material within the core 18 during positioning of the electrode element 2. Although a closure of the cap may offer some advantages in avoiding collection of material within the open hole, it will act to slow the dissolution at least somewhat, and therefore is not preferred. The outside diameter A of the cap 12, the outside diameter (not specifically shown) of the electrode 4 and the collar 8 may be within the same general range of values, at about at least 0.001 inches, preferably from 0.002 to 0.25 inches or 0.005 to 0.20 inches, and more preferably from 0.005 to 0.100 inches. The helical element 6 may generally have an outside diameter B of about 0.001 to 0.07 inches, and an inside diameter C of from about 0.00075 to 0.008 inches. The outside diameter is of course larger than the inside diameter at all times. The central area of the helical element 6 which is defined by the inside diameter C is where the hollow core 18 or the porous material (not shown) within the central area extends. The cap 12 may generally have a length within a range of, for example, 0.05 to 0.25 inches, preferably from 0.09 to 0.15 inches, and more preferably from 0.095 to 0.135 inches. In place of the hollow core 18, a core of more readily dissolvable material (e.g., powdered, frothed or foamed mannitol or equivalent functioning soluble material), may be present. The helical element 6 will have an outside diameter of the dimensions previously noted. It is desirable that the mass of the cap 12 extends below the outside diameter of the helical element 6 rather than merely extending to that outer diameter so that there is some physical gripping by the material of the cap 12 within the helix itself. It is preferred that the mass of the cap extend between the outside diameter and inside diameter of the helical element 6, but it may extend beyond the inside diameter of the helical element 6 and still show improved dissolution rate benefits.

Figure 2:
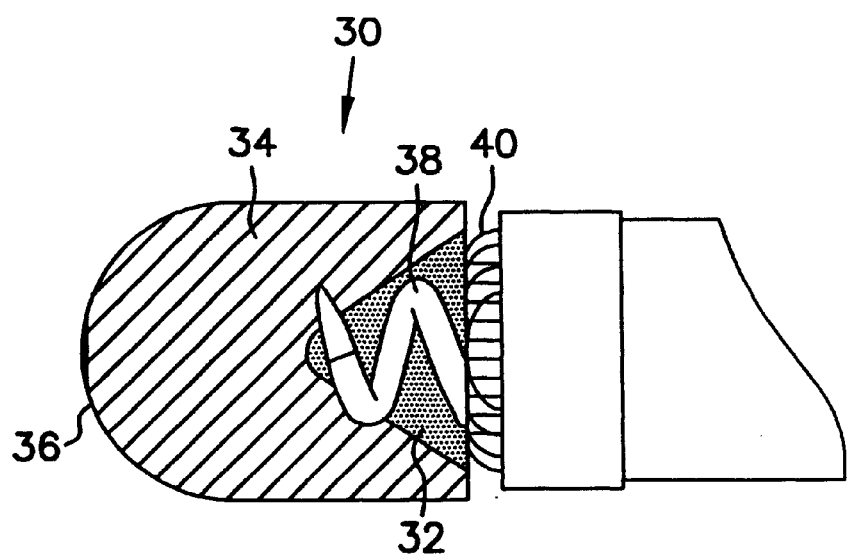
FIG. 2 shows an endocardial lead with a partially dissolved water soluble solid cap.

FIG. 2 shows an electrode element 30 of the prior art with a partially dissolved cap 32. The shaded area 34 represents material from the original cap 36 that has dissolved away, leaving the residue 32 within the helical element 38. It can be readily seen that the remaining core 32 would not only delay the ability of the helical element 38 to be inserted into tissue easily, but also that it would delay the time when the electrode 40 would be in flush electrical contact with tissue (not shown). As the cap would completely dissolve, the temporary presence of these materials merely delays the time when the electrode can be completely secured, but of course, does not affect its actual performance adversely or otherwise. When the cap is prematurely positioned within soft tissue, a mass of mannitol may remain on the tip of the helical element as the last to dissolve material, as opposed to being on the core. This is one reason why the use of a thin cover over the opening to the core is optional.

The article of the present invention may be manufactured as follows. A conventional electrode with a helical insertion tip may be used. A cap may be molded from the blended composition of the water-soluble or water-dispersible component and the hydrogel with the appropriate outside dimensions for the cap. The hollow section of the cap may then be formed, as by drilling, etching, or molding of the appropriate dimensions for the hole (being less than the outside diameter of the helical element). Additionally, a cap may be molded with a hole in the cap material (e.g., as by macaroni extrusion of a continuous tube), with cap sections cut off, and ends of the cap (where desired) closed off to form a closed cap. A Teflon or other release surface center core may be used to mold or extrude the cap material. Where the caps are first molded and a hole added, the hole may be added by selective dissolution of the material to form the hole, drilling or excavating of the hole, or pressing of a heated element into the cap material to remove material. Any method which is capable of producing the caps may be practiced in the present invention. After formation of the cap, the helical element is inserted into the cap, as by twisting or direct line pressure. The cap may be alternatively formed by the following procedures. The helical element is fitted with a removable rod within the core of the helix. A Teflon rod is desirable to assist in the ease of removal. The helical tip with the core therein is dipped or otherwise coated with the dissolvable material. After the cap has been formed by addition of the material onto the tip, the rod is removed. This leaves a hollow core within the helix as desired within the present invention. A more soluble material could be inserted into the helix either by first applying a limited amount of the more soluble material to fill the core of the helix, by pouring the more soluble material into an existing hole (as created by the removal of the rod), or by using a removable rod of more soluble material and not removing it.

Where a porous material is present within the core, rather than a hollow area, the core may either be first formed and the remainder of the cap built upon the porous core or a core excavated from the cap and the porous material added to the hollow area.

One beneficial aspect of the performance of the hollow-core caps of the present invention is the more direct control that the technician has over the timing of the use of the electrodes in the present invention. Not only does the cap dissolve off of the helical element more rapidly, but once there has been partial dissolution of the cap, the forces used to insert the helical element into the tissue cause the residual cap material to break off. When there was a core of material within the central area of the helix, that remaining material could not be broken off by the insertion forces. The technician would have to wait until the residual had been nearly completely dissolved away. These descriptions are intended to be non-limiting and are specific examples of a broadly applicable technology. Other aspects such as tableting of active (e.g., pharmaceutical ingredients, vitamins, anti-inflammatants, etc.) ingredients, and the inclusion of other materials and the use of other processes in accomplishing the objectives of the present invention as enabled herein.

What is claimed:

1. A device for insertion into tissue comprising a helical element with an open central area and a water-soluble or water-dispersible cap for said helical element, the cap for said helical element comprising a mixture of a) a water-soluble or water-dispersible solid and b) a hydrogel.

2. The device of claim 1 wherein the cap has a hollow area which overlaps at least a part of said open central area or a porous water-soluble or water-dispersible composition within at least a portion of said central area.

3. The device of claim 2 wherein said hydrogel is dispersed within the water-soluble or water-dispersible solid.

4. The device of claim 1 wherein said water-soluble or water-dispersible solid comprises a sugar.

5. The device of claim 4 wherein said hydrogel is dispersed within the water-soluble or water-dispersible solid.

6. The device of claim 4 wherein said helical device is coated with an electrically insulating, biocompatible material.

7. The device of claim 1 wherein said water-soluble or water-dispersible solid comprises mannitol.

8. The device of claim 7 wherein said hydrogel is dispersed within the water-soluble or water-dispersible solid.

9. The device of claim 8 wherein said helical element is attached to an electrode.

10. The device of claim 8 wherein the hydrogel is present as a particle dispersion within the water-soluble or water-dispersible component, with the number average particle size of the hydrogel being between 0.5 micrometers and 1 mm.

11. The device of claim 7 wherein the hydrogel is present as a particle dispersion within the water-soluble or water-dispersible component, with the number average particle size of the hydrogel being between 0.5 micrometers and 1 mm.

12. The device of claim 1 wherein said hydrogel is dispersed within the water-soluble or water-dispersible solid.

13. The device of claim 1 wherein said helical element is attached to an electrode.

14. The device of claim 1 wherein said cap comprises a water-soluble or water dispersible carbohydrate.

15. The device of claim 1 wherein said cap comprises a water-soluble or water-dispersible material selected from the group consisting of mannitol, iditol, glucitol, rabitol, heptitol, octitol, arabinitol, betitol, bornesitiol, dambonitol, inositol, laminitol, ononitol, pinitol, sorbitol, non-crosslinked gelatin, and organic polymers.

16. The device of claim 1 wherein said hydrogel comprises a foamed hydrogel.

17. A process for the insertion of an electrical element into the tissue of a patient comprising providing a device according to claim 1, inserting the device into a patient, allowing said cap to contact aqueous bodily fluid within said patient, the hydrogel absorbing said aqueous fluid to swell, and the a water-soluble or water-dispersible solid dissolving or dispersing.

18. The process of claim 17 wherein the cap has a hollow area which overlaps at least a part of said open central area or a porous water-soluble or water-dispersible composition within at least a portion of said central area.

19. The process of claim 17 wherein said water-soluble or water-dispersible solid comprises a carbohydrate.

20. The process of claim 19 wherein said hydrogel is dispersed within the water-soluble or water-dispersible solid.

21. The process of claim 17 wherein said water-soluble or water-dispersible solid comprises mannitol.

22. The process of claim 21 wherein said hydrogel is dispersed within the water-soluble or water-dispersible solid.

23. The process of claim 17 wherein said hydrogel is dispersed within the water-soluble or water-dispersible solid.

24. The process of claim 23 wherein said hydrogel is dispersed within the water-soluble or water-dispersible solid.

25. The device of claim 1 wherein the hydrogel is present as a particle dispersion within the water-soluble or water-dispersible component, with the number average particle size of the hydrogel being between 0.5 micrometers and 1 mm.

* * * * *